US 6,207,099 B1

(12) United States Patent
Rooyakkers et al.

(10) Patent No.: US 6,207,099 B1
(45) Date of Patent: Mar. 27, 2001

(54) PROCESS FOR UNIFORM CROSS-DIRECTION DISTRIBUTION OF PARTICULATE MATERIAL

(75) Inventors: John Anthony Rooyakkers, Little Chute; David Arthur Fell, Neenah; Thomas Joel Halloran, Green Bay; Paul Martin Niemi; Martin Karl Olsen, both of Neenah; Kenneth Raymond Schueler, Jr.; Darold Dean Tippey, both of Appleton, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/421,720

(22) Filed: Oct. 20, 1999

(51) Int. Cl.$^7$ ............................... A61F 13/15; B05B 7/14
(52) U.S. Cl. .................... 264/518; 264/113; 264/121; 425/81.1; 425/83.1
(58) Field of Search .................... 264/518, 113, 264/121; 425/81.1, 83.1

(56) References Cited

U.S. PATENT DOCUMENTS

| | | | |
|---|---|---|---|
| 3,669,831 | 6/1972 | Dupasquier | 162/290 |
| 4,087,508 | 5/1978 | Slaughter et al. | 264/262 |
| 4,432,835 | 2/1984 | Waris et al. | 162/212 |
| 4,551,191 | 11/1985 | Kock et al. | 156/276 |
| 4,585,448 | 4/1986 | Enloe | 604/378 |
| 5,028,224 | 7/1991 | Pieper et al. | 425/80.1 |
| 5,102,585 | 4/1992 | Pieper et al. | 264/37 |
| 5,248,524 | 9/1993 | Soderlund | 427/200 |
| 5,350,597 | 9/1994 | Pelley | 427/197 |
| 5,567,472 | 10/1996 | Siegfried et al. | 427/180 |
| 5,879,751 | 3/1999 | Bogdanski | 427/426 |

FOREIGN PATENT DOCUMENTS

| | | |
|---|---|---|
| 3417700 A1 | 11/1985 | (DE) . |
| 0 072 654 A2 | 2/1983 | (EP) . |
| 0443113 A2 | 8/1991 | (EP) . |
| 2 150 033 | 1/1987 | (GB) . |
| WO 88/04165 A1 | 6/1988 | (WO) . |

OTHER PUBLICATIONS

Sanyo Technical Bulletin, "SAP Sheet," Oct. 1982, pp. 1–3.

Primary Examiner—Mary Lynn Theisen
(74) Attorney, Agent, or Firm—Patricia A. Charlier; Thomas J. Connelly (57) ABSTRACT

A method for forming a substantially uniform distribution of particulate material within a fibrous web includes a conveying step for providing a gas entrained supply of the particulate material. A transferring step directs the particulate material into a delivery gas stream through a delivery conduit and delivery nozzle into a web forming chamber. A fiberizing step provides a flow of a selected fibrous material into the web forming chamber. A foraminous forming layer is disposed within the forming chamber for receiving the fibrous material and the particulate material to produce a fibrous web.

72 Claims, 7 Drawing Sheets

PROCESS FOR UNIFORM CROSS-DIRECTION DISTRIBUTION OF PARTICULATE MATERIAL

THE FIELD OF THE INVENTION

The present invention relates to a method for forming a substantially uniform distribution of particulate material within a fibrous web. More particularly, the present invention relates to a method for forming a substantially uniform distribution of superabsorbent polymer particles within the cross direction of an absorbent pad composed of hydrophilic fibers.

BACKGROUND OF THE INVENTION

Absorbent articles, such as disposable infant diapers, feminine care products, incontinence garments and the like, have included high absorbency superabsorbent polymers to increase the absorbent capacity of the article and to reduce the bulkiness of the article.

Various devices and processes have been employed to manufacture absorbent article designs. Air forming techniques for forming webs of hydrophilic fibers, such as woodpulp fibers, are well known in the art. In addition, it is well known that superabsorbent polymers may be mixed with the hydrophilic fibers during an airlaying process to form an absorbent web. For example, see the Sanyo Technical Bulletin entitled "SAP SHEET", dated October 1982.

Various methods and apparatus have been employed to manufacture absorbent articles. For example, U.K. Patent Application, No. GB 2,150,033 A published Jun. 26, 1985, describes a suction drum apparatus for making an absorbent pad wherein an integrated shell of flocculent material surrounds an internal absorbent layer. U.S. Pat. No. 4,087,508 issued May 2, 1978 to Cook et al. describes a method which includes applying hydrocolloid polymer particles onto the surface of a central zone of a moving web, and distributing the applied particles into the body of the moving web by air-pressure means. International Patent Application No. WO 88/04165 published Jun. 16, 1988 describes a method and apparatus for forming a nonwoven pad consisting of fibrous material in which highly moisture-absorbent particles are intermixed with the fibrous material throughout a predetermined portion of the thickness of the nonwoven pad. It further describes a spray gun or an extension thereof positioned within the chamber relative to the fibrous material atop a conveyor and that is operated to discharge moisture-absorbent material at a predetermined velocity, such that the moisture-absorbent material is intermixed with the fibrous material throughout a central layer of the thickness of the nonwoven pad while forming boundary layers on either side of the center layer which are substantially free of moisture-absorbent material. Additionally, the spray gun preferably operates intermittently to form spaced, sharply defined areas along the length and width of the nonwoven pad wherein each area has moisture absorbent material interspersed throughout a portion of the thickness thereof.

Conventional methods, such as those described above, have not been sufficiently satisfactory. For example, the methods may be overly complex and expensive and may not provide desired uniform deposition for particulate materials, such as superabsorbent granules. The rate of delivery of the superabsorbent particles may not be adequately controlled, and the systems may be excessively sensitive to changing bulk densities in the particulate material.

BRIEF DESCRIPTION OF THE INVENTION

The present invention provides a method for forming a substantially uniform (zoned or otherwise) distribution of particulate material within a fibrous web. Generally stated, a method of the present invention may be practiced using an apparatus as described below. The conveying means provides a gas entrained supply stream of the particulate material. The transferring means directs the particulate material into a delivery gas stream to provide a constant or intermittent flow of a selected quantity of particulate material, a delivery conduit, and a delivery nozzle into a web forming chamber. The fiberizing means provides a flow of a selected fibrous material into the web forming chamber, and directing means controls the flow of the particulate material from the delivery conduit, through the delivery nozzle, into the web forming chamber. A foraminous forming layer is disposed within the web forming chamber for receiving the fibrous material and the particulate material to form a fibrous web having a substantially uniform distribution of the particulate material. Such a distribution may include zoned regions having selected, different amounts of the particulate material therein.

The present invention can further provide a method for forming a substantially uniform distribution of particulate material within the cross direction of a fibrous web. In this aspect of the present invention, the method comprises the steps of providing a gas entrained supply stream of the particulate material. The particulate material is transferred into a delivery gas stream to provide a flow of particulate material through a delivery conduit and delivery nozzle into a web forming chamber. A flow of a selected fibrous material is provided into the web forming chamber, and the flow of particulate material from the delivery nozzle into the forming chamber. The fibrous material and particulate material are received on a foraminous forming layer located within the forming chamber to produce a fibrous web.

Another aspect of the present invention is a distinctive absorbent article comprising a substantially unitary web composed of a mass of hydrophilic fibers, and a quantity of superabsorbent polymer particles substantially uniformly located in the cross direction of the fibrous mass. The superabsorbent particles may have a distinctive, non-uniform distribution along a longitudinal, length dimension of the web. The weight percentage of superabsorbent (per unit weight of the combined particles and fiber) also may be non-uniformly distributed along the length dimension and in the thickness dimension. In particular aspects of the present invention, the absorbent article can also include a longitudinal, length-wise particle distribution that is substantially configured in the form of two or more stepped stages.

The present invention can advantageously provide a method which, when compared to conventional devices, can more efficiently substantially uniformly distribute the particulate material within the cross direction of a fibrous web, and can position the particulate material in a manner which is generally independent of the flow of fibrous material employed to form the web. In the present invention, the method provides a substantially uniform cross-direction particulate distribution within the fibrous web. A further advantage of the present invention is that the method can operate at high speeds. The method also prevents the non-uniform distribution of the particulate material within cross direction of the absorbent article wherein the absorbent article includes a region with a zoned application in the machine direction. The method also prevents a non-uniform distribution of the particulate matter within the cross direction of the absorbent article wherein the absorbent article includes a non-uniform basis weight of fibers in the machine direction and cross direction (pocket forming and profiles).

It has been noted that using current method causes a non-uniform distribution of the particulate material in the cross direction.

The distinctive absorbent article of the present invention can advantageously provide a more efficient use of the absorbent material and provide a more effective, localized placement of superabsorbent particles within a web or pad composed of hydrophilic fibers.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE INVENTION

The following detailed description will be made in the context of depositing particulate material 10, such as superabsorbent particles within a web employed to construct an absorbent body for use in a disposable absorbent article 210 such as a disposable diaper. It should be understood, however, that the present invention may also be employed to incorporate other types of particulate material within a mass of hydrophilic or hydrophobic fibers. In addition, it should be readily understood that the present invention may also be employed to produce absorbent bodies for other types of absorbent articles, such as feminine care products, incontinence articles and the like. All of such alternative configurations are contemplated as being within the scope of the present invention.

The present invention is a method that is particularly useful for depositing particulate material 10, such as organic or inorganic high absorbency material (e.g. superabsorbent), within a fibrous web 42. Suitable inorganic high-absorbency materials include, for example, absorbent clays and silica gels. Organic high-absorbency materials can include natural materials, such as agar, pectin, guar gum and peat moss, as well as synthetic materials, such as synthetic hydrogel polymers. Such hydrogel polymers include, for example, carboxymethylcellulose, alkali metal salts of polyacrylic acids, polyacrylamides, polyvinyl ethers, hydroxypropyl cellulose, polyvinyl morpholinone, polymers and copolymers of vinyl sulfonic acid, polyacrylates, polyacrylamides, polyvinyl pyridine and the like. Other suitable polymers include hydrolyzed acrylonitrile grafted starch, acrylic acid grafted starch, and isobutylene maleic anhydride copolymers, and mixtures thereof. The hydrogel polymers are preferably lightly cross-linked to impart desired levels of water insolubility to the material. Crosslinking may, for example, be by irradiation or by covalent, ionic, Van der Waals, or hydrogen bonding. Suitable materials are available from various commercial vendors, such as Dow Chemical Company, Hoechst Celanese Corporation, Allied-Colloid, and Stockhausen. Typically, the high-absorbency material is capable of absorbing at least about 15 times its weight in water, and preferably is capable of absorbing at least between about 25 and about 100 times its weight in water.

The particulate material 10, such as high absorbency superabsorbent particles, may have regular shapes or irregular shapes, such as elongated forms. For example, the particulate material 10 may be configured in the form of granules, flakes, fibers, or the like. The particulate material 10 typically measure from about 50 to about 1000 micrometers in size, preferably measure from about 100 to about 800 micrometers, and more preferably measure from about 200 to about 600 micrometers in size to provide improved processability through the method of the present invention.

Figure 1:
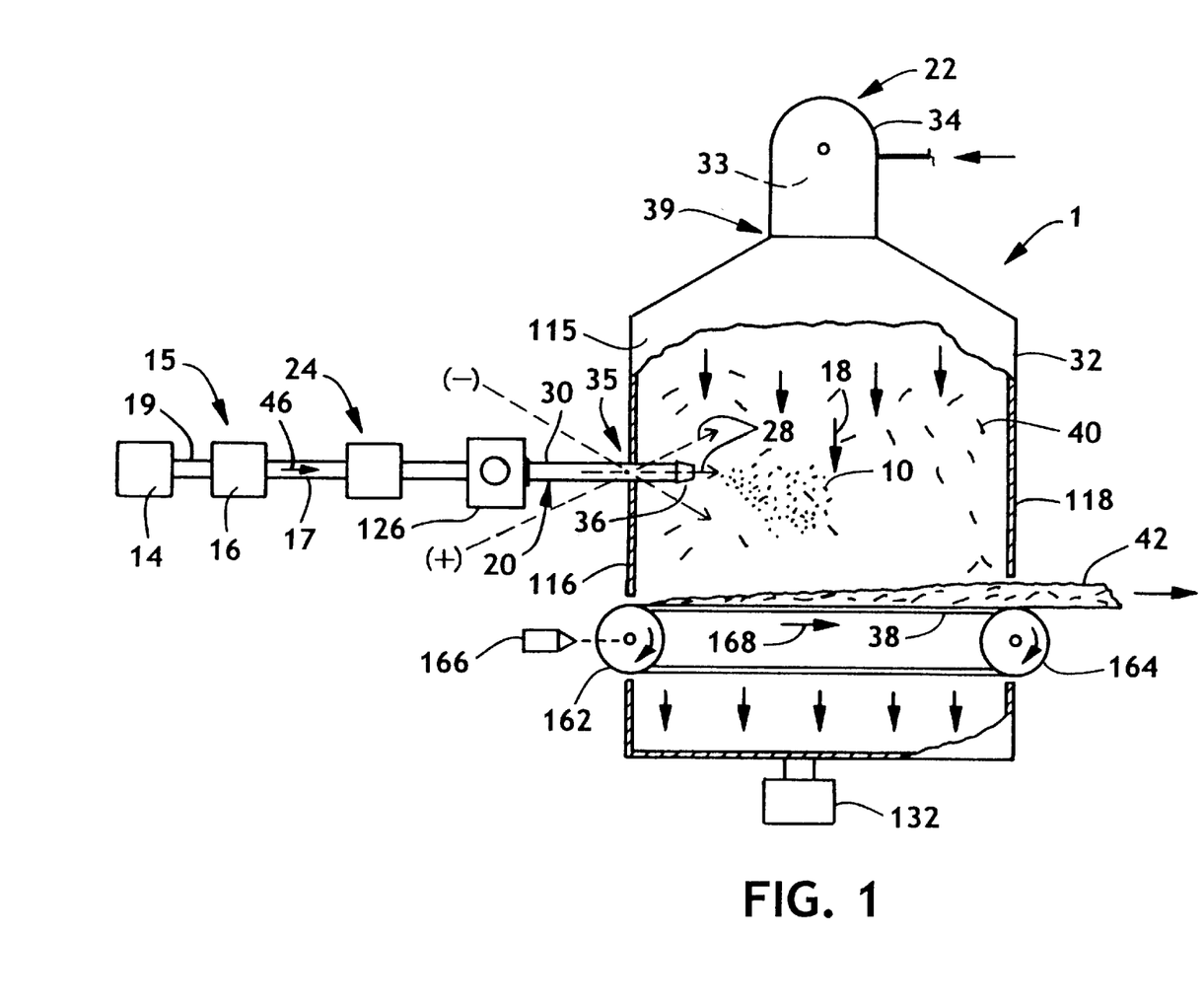
FIG. 1 representatively shows a schematic system diagram of the invention.

With reference to FIG. 1, a representative method of the present invention is configured to form a substantially uniform distribution of particulate material 10, such as particles of a superabsorbent polymer material (SAM), within the cross direction of a fibrous web 42, such as a fibrous web 42 comprising woodpulp fluff fibers 410. A conveying means 15, such as a mechanism composed of the particle feeder device 14 and the conveying blower 16, provides a gas entrained supply stream 18 of the particulate material 10 through a delivery conduit 30 and delivery nozzle 36 into a web forming chamber 32.

The fiberizing means 33, such as the hammermill 34 provides a flow of a selected fibrous material 40, such as woodpulp fluff fibers, into the web forming chamber 32. A directing means 35, such as the delivery nozzle 36, controls the flow (intermittent or otherwise) of the particulate material 10 from the delivery conduit 30 and through the delivery nozzle 36 into web forming chamber 32, and a foraminous forming layer 38 is moveable and disposed within the web forming chamber 32 to receive the fluff fibers 40 and the particulate material 10 thereon to form the fibrous web 42. The fibrous web 42 may include distinctive, zoned regions having selected, different amounts of particulate material 10 therein as disclosed in U.S. Pat. No. 5,102,585 issued to Pieper et al. on Apr. 7, 1992 and U.S. Pat. No. 5,028,224 issued to Pieper et al. on Jul. 2, 1991, incorporated herein by reference. The method of the present invention can advantageously operate at high speeds.

The feeder device 14 includes a particulate regulating means 19 for providing a selected mass flow rate of the particulate material 10, such as high absorbency particles composed of superabsorbent hydrogel polymer, into a conveying gas stream 46 provided by the conveying blower 16. It should be readily understood that the amount of particulate material 10 delivered into the conveying gas stream 46 is dependent upon the forming rate of the fibrous web 42 and the weight percent of the particulate material 10 desired to be contained within the fibrous web 42. In the illustrated embodiment, the particulate regulating means 19 is constructed and configured to provide a particulate mass flow rate which is within the range of about 6–about 400 gm/sec. Various types of feeder mechanisms, such as a feeder device 14, may be employed with the present invention. This feeder device 14 can thereby help control the delivery of the desired amounts of particulate material 10 into the fibrous web 42. In the shown embodiment, the feeder device 14 may be a LWF3-35 feeder manufactured by the K-tron Corp., a company located in Pitman, N.J. Other equivalent feeder devices 14 may also be employed with the present invention.

Various types of commercially available blower devices may be employed with the present invention. In the shown embodiment, conveying blower 16 may be a VB-019 blower manufactured by Spencer Turbine, a company located in Windsor, Conn.

In particular embodiments of the present invention, the conveying blower 16 is configured to supply a conveying gas flow velocity of not less than about 5 m/sec (about 1000 ft/min), and preferably provides a gas velocity of not less than about 9 m/sec (about 1800 ft/min). In other embodiments of the present invention, the conveying blower 16 is configured to provide a gas velocity in the conveying gas stream 46 of not more than about 35 m/sec (about 7000 ft/min), and preferably provides a velocity of not more than about 45 m/sec (about 8500 ft/min) to provide improved performance. A suitable conveying conduit 17 is employed to transport the particle/gas mixture 18 composed of the particulate material 10 entrained in the moving stream of the conveying gas 46.

The proper flow of the conveying gas 46 is dependent on the particulate material 10 being conveyed. In addition to the velocity ranges given, it is desirable to maintain the "solids loading ratio" (mass flow rate of material divided by the mass flow rate of conveying gas) below about 5. Preferably, the solids loading ratio is maintained below about 3. At these ratios, the resultant two-phase flow is typically classified as the "lean phase". The lean phase flow is desirable to minimize short-term weight variability.

FIG. 1 provides a detailed illustration of the web forming chamber 32. The web forming chamber 32 includes a fiber delivery means 39, such as the fiberizer hammermill 34, which provides a flow of the fibrous material 40 within the web forming chamber 32. The foraminous forming layer 38, which is located in the web forming chamber 32 and movable therein, is configured to receive a deposit of the fibrous material 40 thereon. Piping means, such as the delivery conduit 30, and one or more of the delivery nozzles 36, supply a flow of dispersed bodies of particulate material 10, such as the superabsorbent polymer particles. This flow of particulate material 10 enters the web forming chambers 32 and intermixes with the flow of the fibrous material 40 therein. The flow regulating means 20, such as the flow angle adjuster 126, controls the flow vector of the delivery gas stream 28 of the particulate material 10 within the fibrous material 40 deposited onto the forming layer 38 to form the fibrous web 42.

The web forming chamber 32 includes the side walls 115 and the end walls 116 and 118 which are constructed and arranged to define a generally enclosed volume. The end walls 116 and 118 have suitable entrance and exit openings formed therethrough to allow the entry of the forming layer 38 and the removal of the air-formed fibrous web 42 from the web forming chamber 32.

The hammermill 34 may comprise any one of a number of types of conventional fiberizing devices. The sheets of selected fibrous material 40 are typically fed into the hammermill 34, and are disintegrated into a plurality of the individual fibers 40 which are injected or otherwise introduced into the web forming chamber 32. The fibers 40 are typically composed of absorbent, woodpulp fibers commonly referred to as fluff. The fibers 40 may also be composed of staple fibers, polymeric fibers, cellulosic fibers and mixtures thereof, as well as mixtures of absorbent fibers with generally hydrophobic fibers. The fibrous material 40 may optionally be treated to impart desired levels of hydrophilicity, employing techniques well known in the art.

The web forming chamber 32 of the present invention may further include vacuum means 132, such as a conventional blower mechanism, for creating a selected pressure differential through the web forming chamber 32 and past the forming layer 38. The vacuum means 132 is typically located underneath the forming layer 38 to create an air flow through the web forming chamber 32 which is generally directed from the hammermill 34 and past the forming layer 38. This airflow helps to direct and control the deposit of the fibers 40 and the particulate material 10 onto the forming layer 38.

The forming layer 38, for example, may comprise a foraminous forming screen configured as an endless belt which moves about the support rollers 162 and 164. A suitable driving means, such as an electric motor 166, is operably connected to move the forming layer 38 through the web forming chamber 32 at a selected speed along the machine direction 168. The fibers 40 and the particulate material 10 deposit onto the portion of the forming layer 38 within the web forming chamber 32 to form the fibrous web 42, which eventually develops into an absorbent body 240 within an absorbent article 210. Since forming layer 38 moves generally from the end wall 116 toward the exit opening through the end wall 118, the depth or thickness of the fibrous web 42 on any particular section of the forming layer 38 gradually increases as that section of the forming layer 38 traverses through the web forming chamber 32. The fiber deposition rate onto the forming layer 38 and the movement speed of the forming layer 38 can be suitably adjusted to control the finally formed thickness of the air-formed fibrous web 42.

In another aspect of the present invention, the forming layer 38 comprises a foraminous forming screen carrier on an outer circumferential surface of a rotatable drum. A suitable driving means, such as a motor, rotates the drum to move the forming layer 38 through the web forming chamber 32.

Figure 3:
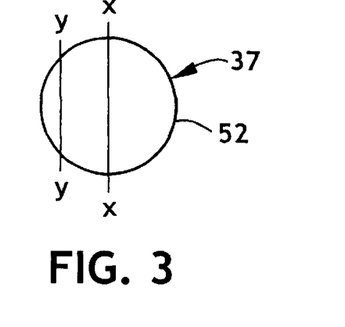
FIG. 3 representatively shows a front view of a current delivery nozzle.
Figure 4:
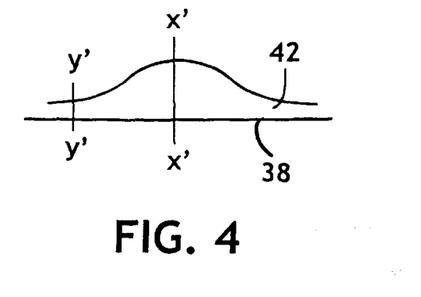
FIG. 4 representatively shows a cross section view of a fibrous web.
Figure 5:
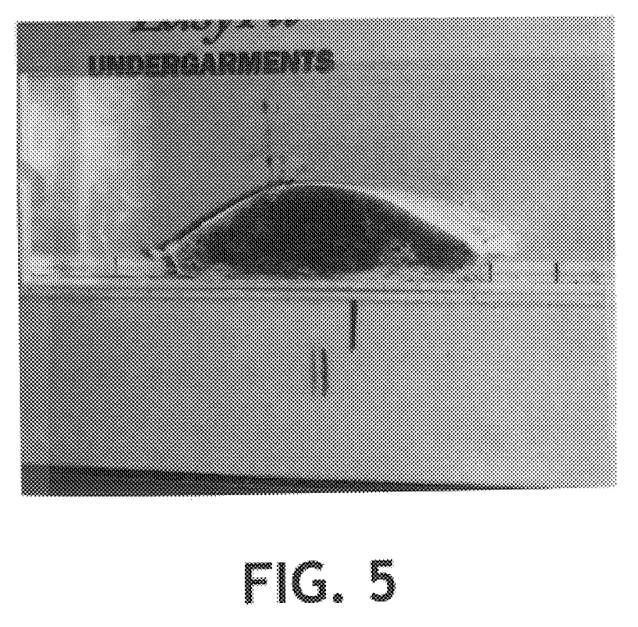
FIG. 5 is a photograph of a cross section view of an absorbent body with the superabsorbent material in a swollen and stained state.

The delivery nozzles 37 currently being used in the industry are typically circular structures as shown in FIG. 3. As the center of the delivery nozzle 37, as shown along the x—x line in FIG. 3, is larger than the side portion of the delivery nozzle 37, as shown along line y—y in FIG. 3, more particulate material 10 is deposited on the corresponding central region of the forming layer 38. (See FIG. 4.) As expected, the corresponding outer portion of the forming layer 38 receives lower amounts of the particulate material 10. This non-uniform distribution of the particulate material 10 is shown in a swollen and stained state in FIG. 5. The absorbent body 240 of the absorbent article 210 is caused to swell by placing the absorbent body 240 in a solution of 0.9% by weight of sodium chloride in water. In addition, the saline solution contains about 0.004 grams per liter of FD&C Blue #1 dye or, in the alternative, enough of the dye to provide the desired level of contrast. The particulate material 10 absorbs a greater amount of the saline solution, and therefore a greater amount of the dye than does the fibrous web 42. As such, the particulate material 10 is a dark blue color as compared to the much lighter blue tint of the fibrous web 42. The particulate material 10 is the darkened lump or bell-curve shaped mass. This non-uniform distribution of the particulate material 10 results in poorer absorbency performance of the absorbent article 210. In addition, as the particulate material 10 swells upon the absorption of fluid, the absorbent body 240 of the absorbent article 210 distorts and can become uncomfortable.

Figure 6:
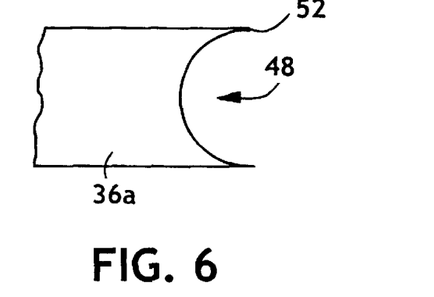
FIG. 6 representatively shows a side view of a delivery nozzle of the present invention.
Figure 7:
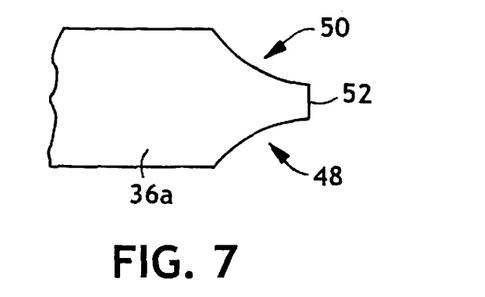
FIG. 7 representatively shows a top view of a delivery nozzle of the present invention.
Figure 8:
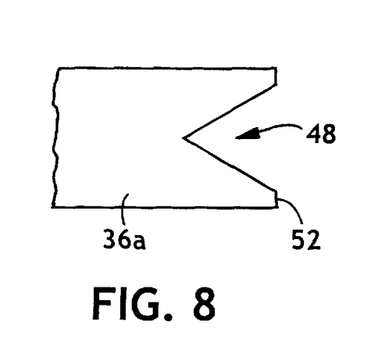
FIG. 8 representatively shows a side view of a delivery nozzle of the present invention.
Figure 9:
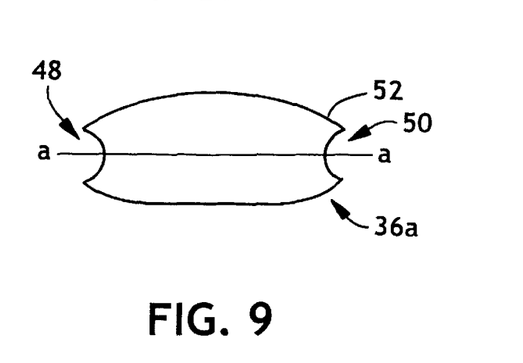
FIG. 9 representatively shows a front view of a delivery nozzle of the present invention.
Figure 10:
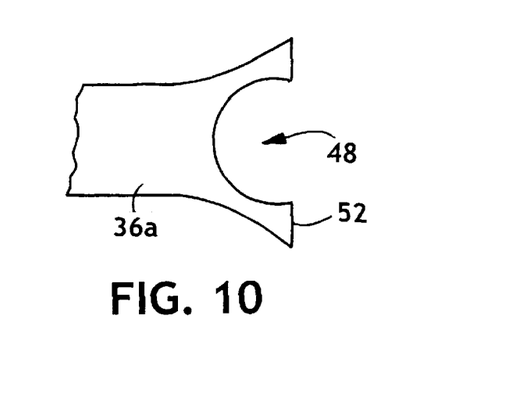
FIG. 10 representatively shows a side view of a delivery nozzle of the present invention.
Figure 11:
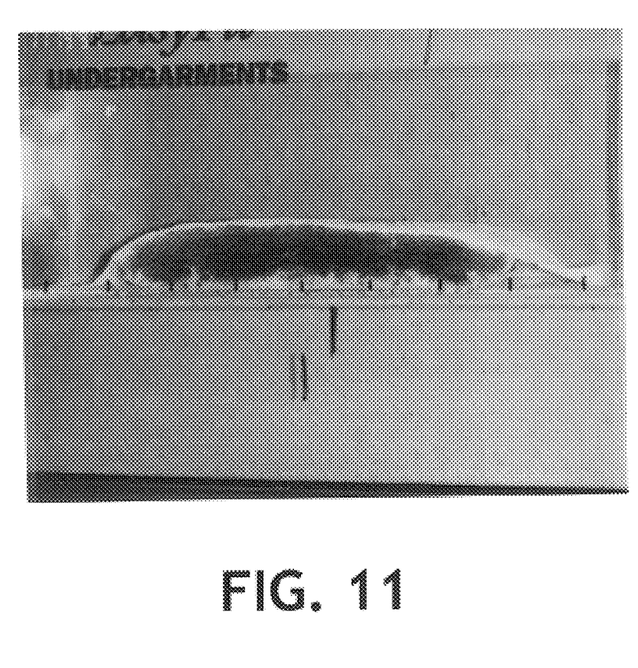
FIG. 11 is a photograph of a cross section of an absorbent body with the superabsorbent material in a swollen and stained state.

It is the geometric shape of the delivery nozzle 36 of the present invention that provides the substantially uniform distribution of the particulate material 10 in the cross direction of the fibrous web 42. One such delivery nozzle 36 that provides a substantially uniform distribution of the particulate material 10 is shown in FIGS. 6, 7, and 8. The delivery nozzle 36a is circular in shape. Side portions of the delivery nozzle 36a have been removed, forming a pair of gaps 48 and 50 in the end edge 52. The gaps 48 and 50 may be semi-circular as shown in FIGS. 6 and 10 or triangular shaped as shown in FIG. 8 or any variation of these designs. The gaps 48 and 50 allow the particulate material 10 to spread out within the web forming chamber 32, thereby avoiding an non-uniform distribution of particulate material 10. The delivery nozzle 36a containing the gaps 48 and 50 may also be oval in shape, having the a—a line parallel to the forming layer 38 as shown in FIG. 9. The resulting substantially uniform distribution of the particulate material 10 resulting from a circular shaped delivery nozzle 36a including gaps 48 and 50 shaped like half circles is shown in a swollen and stained stated in FIG. 11. The particulate material 10 is the darkened oval shaped mass. The end edge 52 of 10 the delivery nozzle 36a may be flared out from the delivery conduit 30 as shown in FIG. 10.

Figure 12:
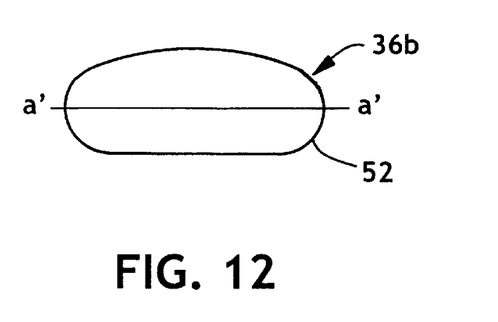
FIG. 12 representatively shows a front view of a delivery nozzle of the present invention.
Figure 13:
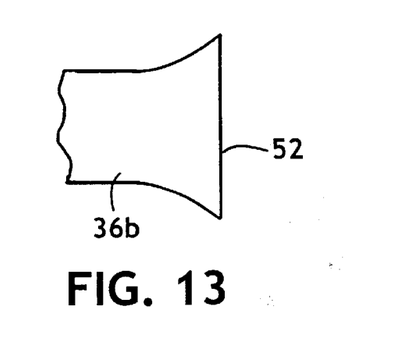
FIG. 13 representatively shows a side view of a delivery nozzle of the present invention.
Figure 14:
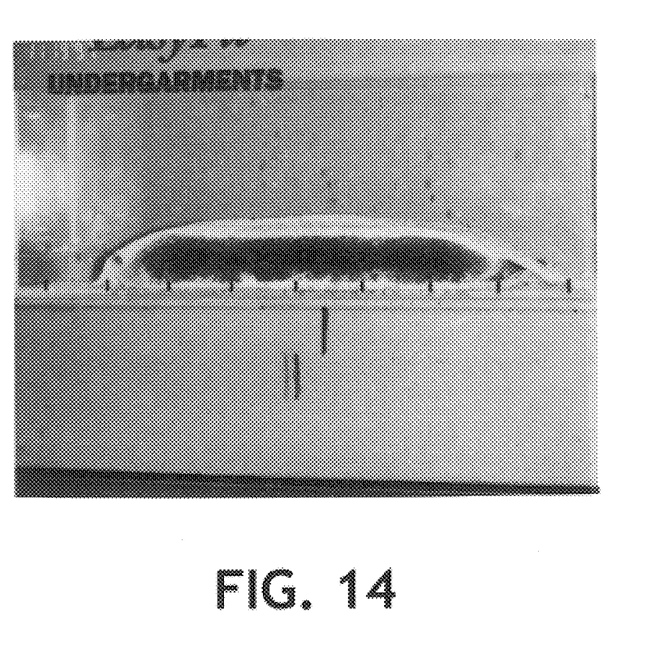
FIG. 14 is a photograph of a cross section of an absorbent body with the superabsorbent material in a swollen and stained state.

Another embodiment of the delivery nozzle 36b that provides a substantially uniform distribution of the particulate material 10 is shown in FIGS. 12 and 13. The delivery nozzle 36b is oval in shape, having the a'—a' line of the delivery nozzle 36b parallel to the forming layer 38. The end edge 52 of the delivery nozzle 36b may flare out from the delivery conduit 30. (See FIG. 13.) The flaring of the end edge 52 further promotes the distribution of the particulate material 10 within the web forming chamber 32. The resulting substantially uniform distribution of the particulate material 10 resulting from an oval shaped delivery nozzle 36b including a flared end edge 52 is shown in a swollen and stained state in FIG. 14. The particulate material 10 is the darkened oval shaped mass.

Figure 15:
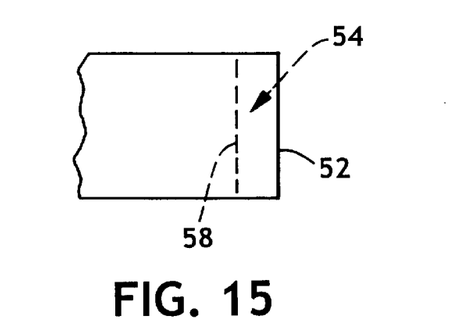
FIG. 15 representatively shows a side view of a delivery nozzle of the present invention.
Figure 16:
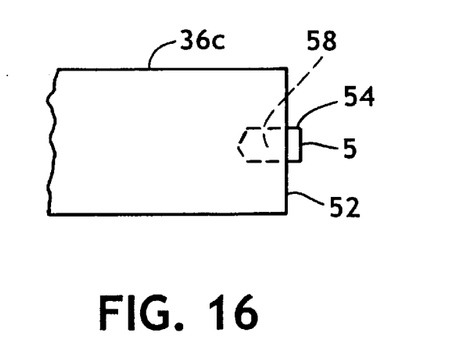
FIG. 16 representatively shows a top view of a delivery nozzle of the present invention.
Figure 17:
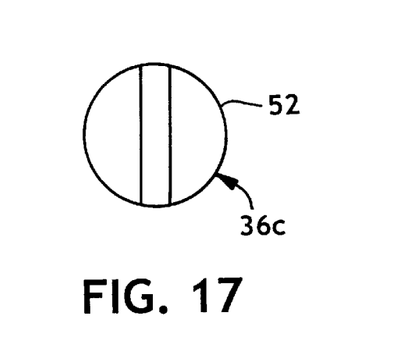
FIG. 17 representatively shows a front view of a delivery nozzle of the present invention.
Figure 18:
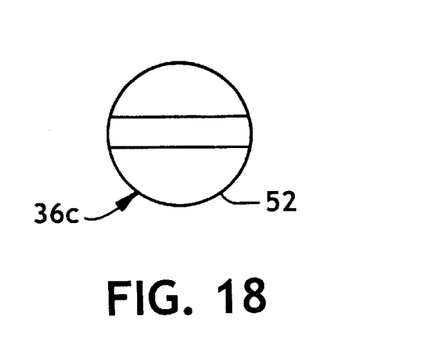
FIG. 18 representatively shows a front view of a delivery nozzle of the present invention.
Figure 19:
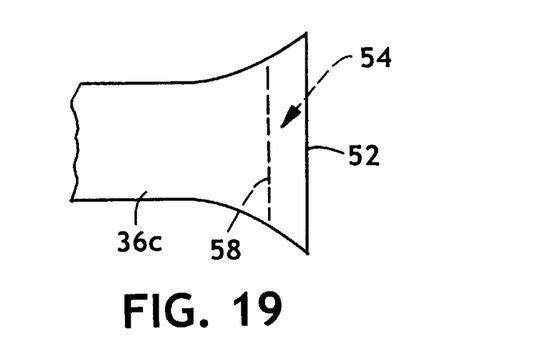
FIG. 19 representatively shows a side view of a delivery nozzle of the present invention.
Figure 20:
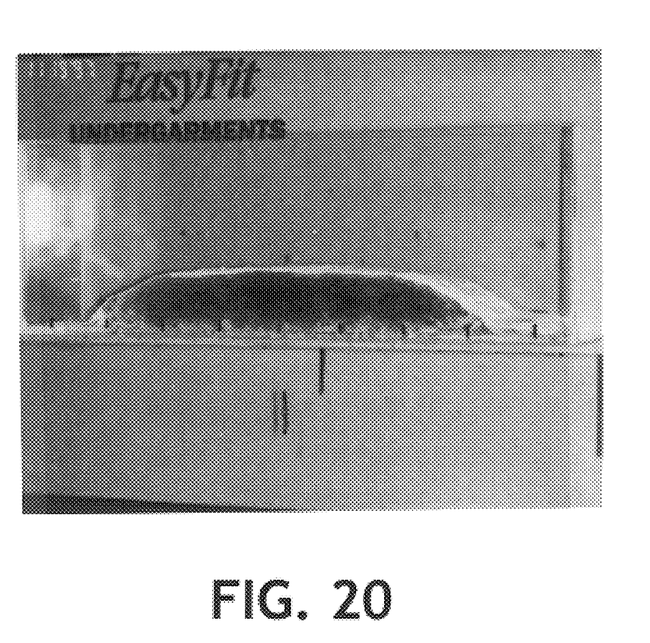
FIG. 20 is a photograph of a cross section of an absorbent body with the superabsorbent material in a swollen and stained state.

Another embodiment of the delivery nozzle 36c that provides a substantially uniform distribution of the particulate material 10 is shown in FIGS. 15, 16, 17, and 18. The delivery nozzle 36c is circular in shape. A wedge member 54, as shown in FIG. 16, is positioned within the delivery nozzle 36c as shown in FIGS. 15 and 16. The wedge member 54 has front face 56 which faces into the web forming chamber 32 and a rear portion 58 that is positioned within the delivery nozzle 36c and may extend into the delivery conduit 30. The wedge member 54 may be rotated through 180° as shown in FIGS. 17 and 18, and any position along the 180° rotation. The rear portion 58 may have a variety of shapes in addition to the shape shown in FIG. 16. The wedge member 54 forces the particulate material 10 toward the sides of the delivery nozzle 36c, resulting in a substantially uniform distribution of particulate material 10, as shown in a swollen and stained state in FIG. 20. The particulate material 10 is the darkened oval shaped mass. The end edge 52 of the delivery nozzle 36c may be flared out from the delivery conduit 30 as shown in FIG. 19.

The present invention may include a single delivery nozzle 36 or may include a multiple delivery nozzle 36 system.

Figure 2:
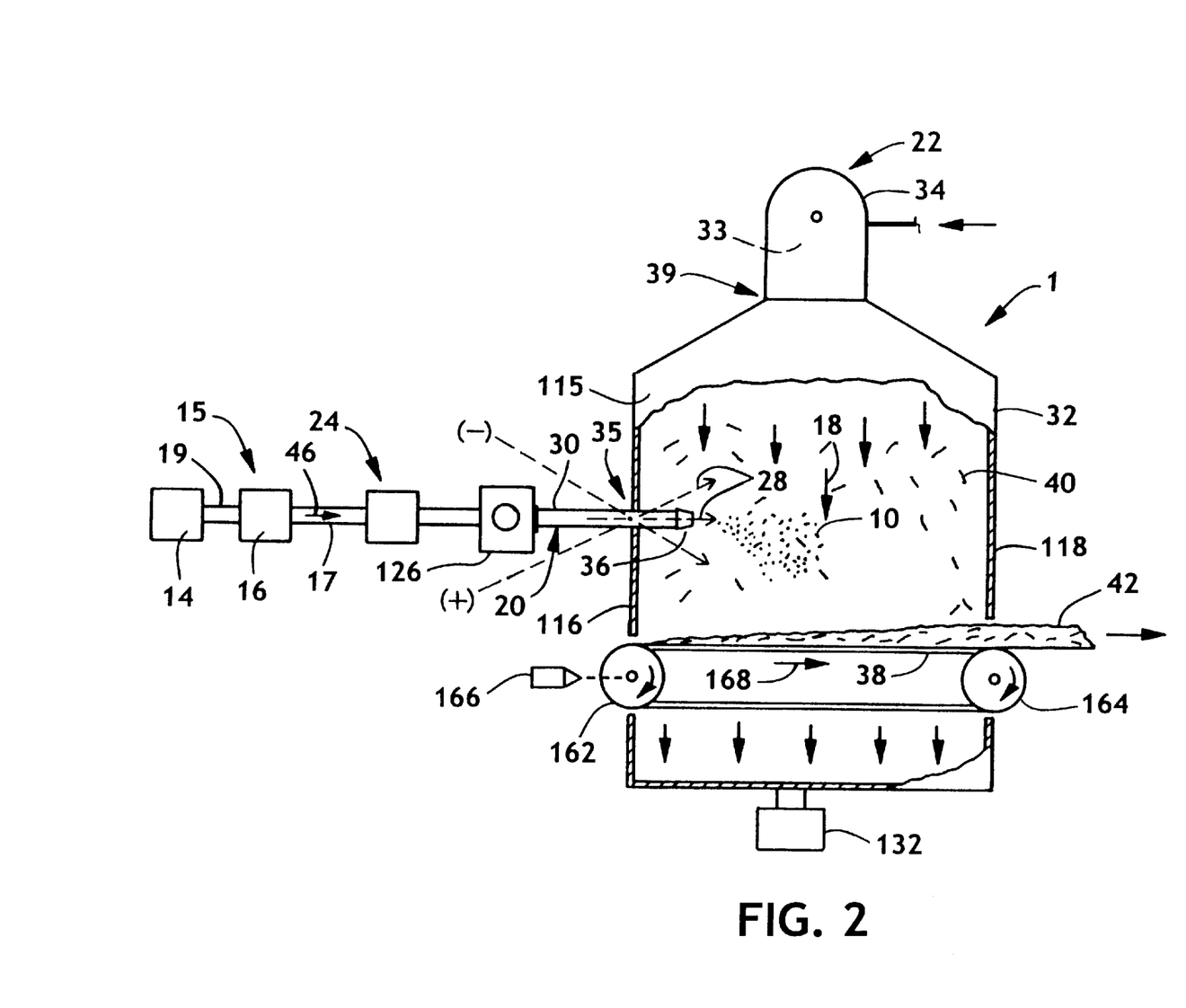
FIG. 2 representatively shows a schematic system diagram of the invention.

Referring again to FIG. 1, the delivery nozzle 36 may protrude into the web forming chamber 32 a predetermined distance to adjust the distribution of particulate material 10 through the thickness of the fibrous web 42. A larger amount of protrusion can, for example, reduce the amount of particulate material 10 deposited near the forming layer side of the fibrous web 42. This design results in a non-uniform distribution of particulate material 10 in the z-direction (throughout the thickness) of the fibrous web 42. As shown in FIG. 2, the delivery nozzle 36 may end flush with the wall 116 of the web forming chamber 32. Such a design results in a more substantially uniform distribution of particulate material 10 in the z-direction of the fibrous web 42.

The delivery nozzle 36 can be suitably adjusted to a nonparallel angle slanted toward or away from the forming layer 38. If the delivery nozzle 36 is angled toward the forming layer 38, relatively more the particulate material 10 can be deposited near the forming layer side of the fibrous web 42. If the delivery nozzle 36 is angled away from the forming layer 38, relatively more the particulate material 10 can be deposited near the upper, free surface side of the fibrous web 42. For example, in a particular aspect of the present invention, the delivery nozzle 36 is constructed and arranged to be pivotable within a range of approximately plus (upwardly) 45° to minus (downwardly) 60°, relative to a plane positioned generally parallel to the forming layer 38. Preferably, the delivery nozzle 36 is pivotable within the range of about plus 10° and minus 45° relative to such plane, respectively away or toward the forming layer 38.

The entry angle of the moving particulate material 10, such as superabsorbent particles can be adjusted by selectively orienting the delivery nozzle 36, and velocities of the particulate material 10 can be appropriately regulated to impart desired, predetermined trajectories to the particulate material 10. As a result, the particulate material 10 can travel different horizontal distances through the web forming chamber 32 in a direction generally parallel to the machine direction of the apparatus. In the illustrated embodiment, the particulate material 10 move along with the movement of the formed fibrous web 42, but in alternative embodiments, the method can be configured to move the particulate material 10 counter to the movement of the fibrous web 42. The difference in horizontal distances can cause differing amounts and/or differing weight percent concentrations of the particulate material 10 to be selectively placed at various desired levels through the thickness dimension of the fibrous web 42.

Particular aspects of the present invention can include combinations of the various, different types systems for delivering the particulate material 10 into the web forming chamber 32.

Figure 21:
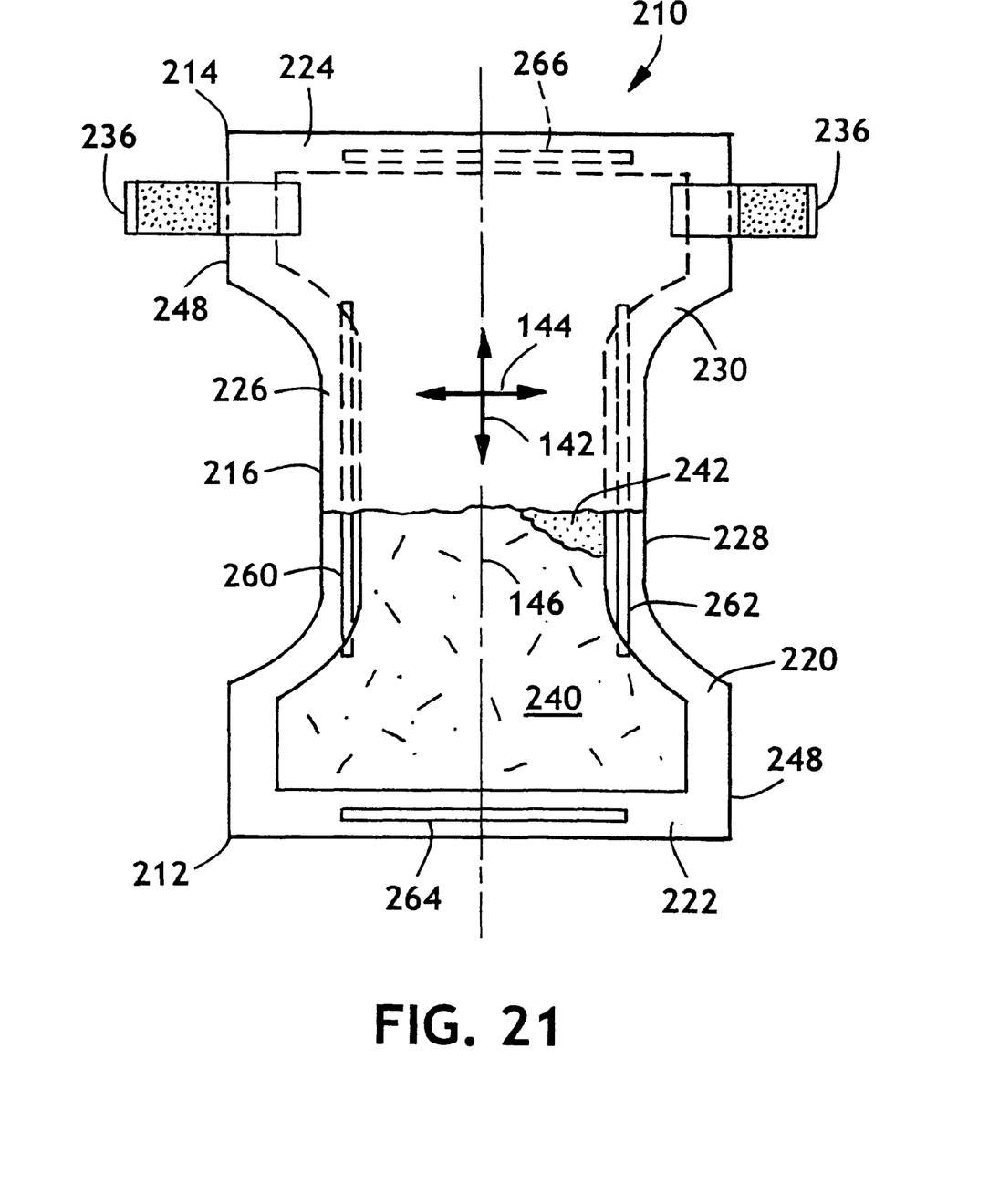
FIG. 21 representatively shows an absorbent diaper-type article which incorporates an absorbent body of the present invention.

With reference to FIG. 21, an integral absorbent garment article 210, such as a disposable diaper, generally delimits a front waistband panel-section 212, a rear waistband panel-section 214, and an intermediate section 216 which interconnects the front and rear waistband sections. The absorbent article 210 comprises a substantially fluid impermeable backsheet layer 220, a liquid permeable topsheet layer 230 positioned in facing relation with the backsheet layer 220, and an absorbent body 240 is located between the backsheet layer 220 and the topsheet layer 230. For reference purposes, the absorbent article 210 has a longitudinal direction 142, a cross-direction 144 and a longitudinal centerline 146.

The marginal portions of the absorbent article 210, such as the marginal sections of the backsheet 220, may extend past the terminal edges of the absorbent body 240 which includes the fibrous web 242. In the illustrated embodiment, for example, backsheet 220 extends outwardly beyond the terminal marginal edges of the absorbent body 240 to form the garment side margins 226 and 228 and the garment end margins 222 and 224. The topsheet 230 is generally coextensive with the backsheet 220, but may optionally cover an area which is larger or smaller than the area of the backsheet 220, as desired.

The absorbent article 210 may be of various suitable shapes. For example, the absorbent article 210 may have an overall rectangular shape, T-shape or an approximately hour-glass shape. In the shown embodiment, the absorbent article 210 as a generally I-shape.

The various components of the absorbent article 210 are integrally assembled together employing various types of suitable attachment means, such as adhesive, ultrasonic bonds, thermal bonds, and the like, and combinations thereof. In the shown embodiment, for example, the topsheet 230 and the backsheet 220 are assembled to each other and to the absorbent body 240 with lines and patterns of adhesive, such as a hot melt, pressure-sensitive adhesive. Similarly, other absorbent article 210 components, such as the elastic members 260, 262, 264, and 266 and the fastening members 236, may be assembled into the absorbent article 210 by employing the above-identified attachment mechanisms.

The illustrated embodiment of the absorbent article 210 includes the ear portions 248, which extend laterally along the absorbent article cross-direction 144 and are positioned at least at one waistband section of the absorbent article 210, preferably at the rear waistband section 214. The ear portions 248 may also be located at the front waistband section 212 of the absorbent article 210. The ear portions 248 may be integral with backsheet layer 220, or may comprise separate sections, which are composed of the same or different material than the backsheet layer 220 and are suitably assembled and attached to the backsheet layer 220. The ear sections 248 typically provide extensions of the absorbent article waistband suitable for completely encircling the waist of the wearer during use.

The fastening means 236, such as adhesive tapes, are employed to secure the absorbent article 210 on a wearer. Alternatively, other fastening means, such as buttons, pins, snaps, hook-and-loop fasteners, mushroom-and-loop fasteners, or the like, may be employed.

To provide an improved fit and to help reduce leakage of body exudates from absorbent article 210, the side margins 226 and 228 and the end margins 222 and 224 may be elasticized with the suitable elastic members 260 and 262, such as single or multiple strands of elastic. The elastic members 260 and 262 may be composed of natural or synthetic rubber or other elastomeric materials, and may optionally be heat shrinkable or heat-elasticizable. The elastic members 260 and 262 are constructed to operably gather and shirr the side margins 226 and 228 to provide elasticized leg bands which can closely fit around the legs of the wearer to reduce leakage and provide improved comfort and appearance. Similarly, the waist elastic members 264 and 266 can be employed to elasticize the end margins 222 and 224 to provide elasticized waistbands. The waist elastics 264 and 266 are configured to operably gather and shirr the waistband sections to provide a resilient, comfortably close fit around the waist of the wearer.

The backsheet layer 220 is composed of a substantially liquid impermeable material, which is also gas impermeable but may optionally be gas/vapor permeable. In the illustrated embodiment, the backsheet layer 220 is substantially impermeable to water and water vapor. An example of a suitable backsheet material is a polymer film composed of polyethylene, polypropylene, or the like. Typically, the polymer film has a thickness within the range of about 0.0004–about 0.002 inch (0.0010–0.0051 cm). The backsheet layer 220 may alternatively be composed of a nonwoven fibrous web constructed to provide the desired levels of fluid impermeability. For example, a nonwoven web composed of spunbonded or meltblown polymer fibers may be selectively treated with a water repellent coating, or laminated with a fluid impermeable, polymer film.

In alternative embodiments of the present invention, the backsheet layer 220 may comprise a nonwoven web composed of a plurality of randomly deposited hydrophobic thermoplastic meltblown fibers which are sufficiently bonded or otherwise connected to one another to provide a substantially vapor impermeable and substantially liquid impermeable web. The backsheet layer 220 may also comprise a vapor permeable nonwoven layer which has been partially coated or otherwise configured to provide liquid impermeability only in selected areas, leaving the remaining areas vapor permeable.

The topsheet 230 is typically composed of a liquid permeable, substantially hydrophobic fibrous material, such as a spunbonded web composed of synthetic polymer filaments. Alternatively, the topsheet 230 may comprise a meltblown web or a bondedcarded-web composed of synthetic polymer filaments. Suitable synthetic polymers include, for example, polyethylene, polypropylene and polyesters. In a particular aspect of the invention, the polymer filaments have a denier within the range of about 1.5 to about 7 d and preferably have a denier within the range of about 1.5 to about 3 d to provide improved performance. The filaments are arranged to form a layer having a basis weight within the range of about 8 to about 34 gm/m2 (gsm), and preferably are arranged to have a basis weight of about 27 gsm.

The topsheet 230 may optionally be treated with surfactants to adjust its degree of hydrophobicity and wettability. It can also be selectively embossed or apertured with discrete slits or holes 232 extending therethrough.

The absorbent body 240 comprises an integral mass of hydrophilic material which is typically configured to form a fibrous absorbent pad layer. The hydrophilic fibers can, for example, be composed of a fibrous cellulosic material commonly referred to as woodpulp fluff, and can be air-formed to form an integral fibrous pad. Other fibers, such as cotton and synthetic polymer fibers, may also be employed to form the pad. Conventional absorbent pads can have a density ranging from about 0.05 to about 0.50 grams/cc, preferably 0.08 to about 0.3 grams/cc, more preferably 0.12 to about 0.20 grams/cc, and are sufficiently flexible to readily conform to the body shape of the wearer. In particular arrangements, the fibrous material comprising the absorbent body 240 may be non-uniformly distributed over the pad length and width. For example, see U.S. Pat. No. 4,585,448, "Disposable Garment Having High-Absorbency Area", issued Apr. 29, 1986 to K. Enloe.

To increase the absorbent capacity of the absorbent body 240, it has been desirable to add quantities of relatively high-absorbency material to the fibers comprising the absorbent body 240. Such high-absorbency materials are capable of holding, on a weight basis, at least about 15 parts of water per part of high-absorbency material. Preferably, the high absorbency material is capable of holding at least about 100 parts of water per part of high-absorbency material.

The absorbent body 240 should include an effective amount of the high-absorbency material to operably enhance the absorptive capacity of the absorbent body 240. For example, the absorbent body 240 can contain between about 5 to about 95 weight percent high-absorbency material, and preferably includes between about 10 to about 50 weight percent of the high-absorbency material to provide more efficient performance.

The high-absorbency material has typically been distributed or otherwise incorporated into the absorbent body 240 by employing various techniques. For example, the high-absorbency material can be incorporated into a separate carrier sheet which is layered with a body of air-formed cellulosic fibers. Alternatively, the high-absorbency material may be substantially uniformly distributed in the z-direction and mixed within the mass of fibers comprising the absorbent body 240. The material can also be non-uniformly distributed in the z-direction among the fibers to form, for example, a generally continuous gradient with either an increasing or decreasing concentration of high-absorbency material, as determined by observing the concentration moving from the body-side of the absorbent body 240 toward the outer-side of the absorbent body 240. The high-absorbency material may also be substantially unmixed with the fibrous material of the absorbent body 240, and may comprise one or more discrete layers or strips selectively segregated from the fibrous material.

Optionally, a substantially hydrophilic tissue wrap 242 may be employed to help maintain the integrity of the air-formed fibrous structure of the absorbent body 240. The tissue wrap 242 is typically placed about the absorbent body 240 over at least the two major facing surfaces thereof, and composed of an absorbent cellulosic material, such as creped wadding or a high wet-strength tissue.

In a particular aspect of the present invention, the absorbent body 240 has the structural configuration of a concurrently air-formed mixture of hydrophilic fibers and particulate material 10. The fibers and particulate material 10 are concurrently formed into a substantially integral web layer while the fibers and particulate material 10 are intermingled with each other. In such structure, the particulate material 10 is not substantially isolated in a discrete superabsorbent layer. The resultant absorbent body 240 can include a distinctive, selectively varied distribution of the particulate material 10 along the longitudinal length dimension 142 of the absorbent body 240. For example, the average weight percentage of particulate material 10 can be non-uniformly distributed along said length dimension.

The intermixed configuration of the particulate material 10 and fibrous material is desirable because it can provide an advantageous combination of capillarity, interfiber void volume and total absorbent capacity. The fibrous material contributes to the capillarity and interfiber void volume, while the particulate material 10 contribute to the total absorbent capacity. The fiber capillarity helps provide a rapid movement and wicking of liquid through the absorbent body 240 and the interfiber void volume helps provide a rapid rate of liquid uptake into the absorbent body 240. In addition, the intermingled configuration of the particulate material 10 and fibrous material helps improve the mechanical integrity of the total structure.

The method of the present invention for forming a substantially uniform distribution of particulate material 10 in the cross-machine direction within a fibrous web 42, comprises the steps of:

(a) providing a gas entrained supply stream 18 of the particulate material 10;

(b) transferring a selected quantity of the particulate material 10 into a delivery gas stream 28 to provide a flow of the particulate material 10 through a delivery conduit 30 and a delivery nozzle 36b, including an end edge 52 and having an oval shape, into a web forming chamber 32;

(c) providing a flow of a selected fibrous material 40 into the web forming chamber 32; and, (d) receiving the fibrous material 40 and the particulate material 10 on a foraminous forming layer 38 located within the web forming chamber 32 to produce a fibrous web 42 which includes a substantially uniform distribution of the particulate material 10.

The method may further comprise the step of positioning the delivery nozzle 36b to provide a substantially uniform distribution of the particulate material 10 the cross direction of the fibrous web. The end edge 52 of the delivery nozzle 36b may flare out from the delivery conduit 30. The method may further comprise the step of positioning the delivery nozzle 36b to provide a substantially uniform distribution of the particulate material 10 in the cross direction 144 of the fibrous web 42. The providing step may include the steps of generating a stream 46 of conveying gas for entraining the particulate material 10 and regulating a flow of the conveying gas 46 to provide a gas flow velocity within the range of about 5 m/sec to about 45 m/sec. The method may further comprise the steps of providing the delivery gas stream 28 and regulating a flow of the delivery gas stream 28 to provide a velocity of gas flow within the range of about 5 m/sec to about 45 m/sec. The method may further comprise a step of providing a selected, regulated mass flow rate of the particulate material 10 within the supply stream 18.

The method may further comprise the step of controlling the flow of the particulate material 10 from the delivery conduit 30 and the delivery nozzle 36b into the forming chamber 32. The transferring step may comprise the steps of delivering a controlled quantity of the particulate material 10 to the delivery conduit 30 and providing the delivery stream 28 of gas at a selected velocity to move the particulate material 10 through the delivery conduit 30. The method may further comprise a step of directing a substantially continuous stream of particulate material 10 into the web forming chamber 32. The selective transferring step may comprise the steps of directing a first particulate material 10 into the web forming chamber 32 with a first transferring means; and, directing at least a second particulate material 10 into the web forming chamber 32 with a second transferring means. In the alternative, the method may further comprise a step of directing an intermittent stream of particulate material 10 into the web forming chamber 32.

Another embodiment of the method of the present for forming a substantially uniform distribution of particulate material 10 in the cross-machine direction within a fibrous web 42, comprising the steps of:

(a) providing a gas entrained supply stream 18 of the particulate material 10;

(b) transferring a selected quantity of the particulate material 10 into a delivery gas stream 28 to provide a flow of the particulate material 10 through a delivery conduit 30 and a delivery nozzle 36a, including an end edge 52 and having a circular shape including gaps 48 and 50 on the end edge 52 facing into a web forming chamber 32, into a web forming chamber 32;

(c) providing a flow of a selected fibrous material 40 into the web forming chamber 32; and, (d) receiving the fibrous material 40 and the particulate material 10 on a foraminous forming layer 38 located within the forming chamber 32 to produce a fibrous web 42 which includes a substantially uniform distribution of the particulate material 10.

The method may further comprise the step of positioning the delivery nozzle 36a to provide a substantially uniform distribution of the particulate material 10 in the cross direction 144 of the fibrous web 42. The end edge 52 of the delivery nozzle 36a may flare out from the delivery conduit 30. The method may further comprise the step of positioning the delivery nozzle 36a to provide a substantially uniform distribution of the particulate material 10 in the cross direction 144 of the fibrous web 42. The gaps 48 and 50 in the end edge 52 of the delivery nozzle 36a may be semi-circular in shape or triangular in shape. The providing step may include the steps of generating a stream 46 of conveying gas for entraining the particulate material 10 and regulating a flow of the conveying gas 46 to provide a gas flow velocity within the range of about 5 m/sec to about 45 m/sec. The method may further comprise steps of providing the delivery gas stream 28 and regulating a flow of the delivery gas stream 28 to provide a velocity of gas flow within the range of about 5 m/sec to about 45 m/sec. The method may further comprise a step of providing a selected, regulated mass flow rate of the particulate material 10 within the supply stream 18. The method may further comprise the step of controlling the flow of the particulate material 10 from the delivery conduit 30 and the delivery nozzle 36a into the forming chamber 32.

The transferring step may comprise steps of delivering a controlled quantity of the particulate material 10 to the delivery conduit 30 and providing the delivery stream 28 of gas at a selected velocity to move the particulate material 10 through the delivery conduit 30. The method may further comprise a step of directing a substantially continuous stream of particulate material 10 into the web forming chamber 32. In the alternative, the method may further comprise a step of directing an intermittent stream of particulate material 10 into the web forming chamber 32.

The selective transferring step comprises the steps of directing a first particulate material 10 into the web forming chamber 32 with a first transferring means and directing at least a second particulate material 10 into the web forming chamber 32 with a second transferring means.

Another embodiment of the method of the present invention for forming a substantially uniform distribution of particulate material 10 in the cross-machine direction 144 within a fibrous web 42, comprising the steps of:

(a) providing a gas entrained supply stream 18 of the particulate material 10;

(b) transferring a selected quantity of the particulate material 10 into a delivery gas stream 28 to provide a flow of the particulate material 10 through a delivery conduit 30 and a delivery nozzle 36b, including an end edge 52 and having a oval shape including gaps 48 and 50 on the end edge 52 facing into a web forming chamber 32, into a web forming chamber 32;

(c) providing a flow of a selected fibrous material 40 into the web forming chamber 32; and, (d) receiving the fibrous material 40 and the particulate material 10 on a foraminous forming layer 38 located within the forming chamber 32 to produce a fibrous web 42 which includes a substantially uniform distribution of the particulate material 10.

The method may further comprise the step of positioning the delivery nozzle 36b to provide a substantially uniform distribution of the particulate material 10 in the cross direction 144 of the fibrous web 42. The end edge 52 of the delivery nozzle 36b may flare out from the delivery conduit 30. The method may further comprise the step of positioning the delivery nozzle 36b to provide a substantially uniform distribution of the particulate material 10 in the cross direction 144 of the fibrous web 42. The gaps 48 and 50 in the end edge 52 of the delivery nozzle 36b may be semi-circular in shape or triangular in shape. The providing step may include the steps of generating a stream 46 of conveying gas for entraining the particulate material 10 and regulating a flow of the conveying gas to provide a gas flow velocity within the range of about 5 m/sec to about 45 m/sec. The method may further comprise steps of providing the delivery gas stream 28 and regulating a flow of the delivery gas stream 28 to provide a velocity of gas flow within the range of about 5 m/sec to about 45 m/sec. The method may further comprise a step of providing a selected, regulated mass flow rate of the particulate material 10 within the supply stream 18. The method may further comprise the step of controlling the flow of the particulate material 10 from the delivery conduit 30 and the delivery nozzle 36b into the forming chamber 32.

The transferring step may comprises steps of delivering a controlled quantity of the particulate material 10 to the delivery conduit 30 and providing the delivery stream 28 of gas at a selected velocity to move the particulate material 10 through the delivery conduit 30. The method may further comprise a step of directing a substantially continuous stream of particulate material 10 into the web forming chamber 32. In the alternative, the method may further comprise a step of directing an intermittent stream of particulate material 10 into the web forming chamber 32.

The selective transferring step comprises the steps of directing a first particulate material 10 into the web forming chamber 32 with a first transferring means arid directing at least a second particulate material 10 into the web forming chamber 32 with a second transferring means.

Another embodiment of the method of the present invention for forming a substantially uniform distribution of particulate material 10 in the cross-machine direction 144 within a fibrous web 42, comprising the steps of:

(a) providing a gas entrained supply stream 18 of the particulate material 10;

(b) transferring a selected quantity of the particulate material 10 into a delivery gas stream 28 to provide a flow of the particulate material 10 through a delivery conduit 30 and a delivery nozzle 36c, including an end edge 52 and a wedge member 54 wherein the delivery nozzle 36c is circular shaped, into a web forming chamber 32;

(c) providing a flow of a selected fibrous material 40 into the web forming chamber 32; and, (d) receiving the fibrous material 40 and the particulate material 10 on a foraminous forming layer 38 located within the forming chamber 32 to produce a fibrous web 42 which includes a substantially uniform distribution of the particulate material 10.

The method may further comprise the step of positioning the delivery nozzle 36 to provide a substantially uniform distribution of the particulate material 10 in the cross direction of the fibrous web. The end edge 52 of the delivery nozzle 36c may flare out from the delivery conduit 30. The method may further comprise the step of positioning the delivery nozzle 36 to provide a substantially uniform distribution of the particulate material 10 in the cross direction 144 of the fibrous web 42. The providing step may include the steps of generating a stream 46 of conveying gas for entraining the particulate material 10 and regulating a flow of the conveying gas 46 to provide a gas flow velocity within the range of about 5 m/sec to about 45 m/sec. The method may further comprise the steps of providing the delivery gas stream 28 and regulating a flow of the delivery gas stream 28 to provide a velocity of gas flow within the range of about 5 m/sec to about 45 m/sec. The method may further comprise a step of providing a selected, regulated mass flow rate of the particulate material 10 within the supply stream 18.

The method may further comprise the step of controlling the flow of the particulate material 10 from the delivery conduit 30 and the delivery nozzle 36c into the forming chamber 32. The transferring step may comprise the steps of delivering a controlled quantity of the particulate material 10 to the delivery conduit 30 and providing the delivery stream 28 of gas at a selected velocity to move the particulate material 10 through the delivery conduit 30. The method may further comprise a step of directing a substantially continuous stream of particulate material 10 into the web forming chamber 32. In the alternative, the method may further comprise a step of directing an intermittent stream of particulate material 10 into the web forming chamber 32. The selective transferring step may comprise the steps of directing a first particulate material 10 into the web forming chamber 32 with a first transferring means; and, directing at least a second particulate material 10 into the web forming chamber 32 with a second transferring means.

Having thus described the invention in rather full detail, it will be readily apparent to a person having ordinary skill in the art that various changes and modifications can be made without departing from the spirit of the invention. All of such changes and modifications are contemplated as being within the scope of the present invention, as defined by the subjoined claims.

We claim:

1. A method for forming a substantially uniform distribution of particulate material in the cross-machine direction within a fibrous web, comprising the steps of:
    (a) providing a gas entrained supply stream of said particulate material;
    (b) transferring a selected quantity of said particulate material into a delivery gas stream to provide a flow of said particulate material through a delivery conduit and a delivery nozzle, including an end edge and having an oval shape, into a web forming chamber;
    (c) providing a flow of a selected fibrous material into said web forming chamber; and,
    (d) receiving said fibrous material and said particulate material on a foraminous forming layer located within said web forming chamber to produce said fibrous web which includes a substantially uniform distribution of said particulate material.

2. The method as recited in claim 1, further comprising the step of positioning said delivery nozzle to provide a substantially uniform distribution of said particulate material in the cross direction of said fibrous web.

3. The method as recited in claim 1, wherein said end edge of said delivery nozzle flares out from the delivery conduit.

4. The method as recited in claim 3, further comprising the step of positioning said delivery nozzle to provide a substantially uniform distribution of said particulate material in the cross direction of said fibrous web.

5. The method as recited in claim 1, wherein said providing step (a) includes steps of:
    generating a stream of conveying gas for entraining said particulate material; and,
    regulating a flow of said conveying gas to provide a gas flow velocity within the range of about 5 m/sec to about 45 m/sec.

6. The method as recited in claim 5, further comprising steps of:
    providing said delivery gas stream; and,
    regulating a flow of said delivery gas stream to provide a velocity of gas flow within the range of about 5 m/sec to about 45 m/sec.

7. The method as recited in claim 6, further comprising a step of providing a selected, regulated mass flow rate of said particulate material within said supply stream.

8. The method as recited in claim 1, further comprising the step of controlling said flow of said particulate material from said delivery conduit and said delivery nozzle into said web forming chamber.

9. The method as recited in claim 1, wherein said transferring step (b) comprises steps of:
    delivering a controlled quantity of said particulate material to said delivery conduit; and,
    providing said delivery stream of gas at a selected velocity to move said particulate material through said delivery conduit.

10. The method as recited in claim 9, further comprising a step of directing a substantially continuous stream of particulate material into said web forming chamber.

11. The method as recited in claim 1, further comprising a step of directing a substantially continuous stream of particulate material into said web forming chamber.

12. The method as recited in claim 1, further comprising the step of directing an intermittent stream of particulate material into said web forming chamber.

13. The method as recited in claim 1, wherein said selective transferring step (b) comprises the steps of:
    directing a first particulate material into said web forming chamber with a first transferring means; and,
    directing at least a second particulate material into said web forming chamber with a second transferring means.

14. A method as recited in claim 13, further comprising the step of directing a substantially continuous stream of particulate material into said web forming chamber.

15. A method for forming a substantially uniform distribution of particulate material in the cross-machine direction within a fibrous web, comprising the steps of:
    (a) providing a gas entrained supply stream of said particulate material;
    (b) transferring a selected quantity of said particulate material into a delivery gas stream to provide a flow of said particulate material through a delivery conduit and a delivery nozzle, including an end edge and having a circular shape including gaps on the end edge facing into a web forming chamber, into said web forming chamber;

(c) providing a flow of a selected fibrous material into said web forming chamber; and, (d) receiving said fibrous material and said particulate material on a foraminous forming layer located within said forming chamber to produce said fibrous web which includes a substantially uniform distribution of said particulate material.

16. The method as recited in claim 15, further comprising the step of positioning said delivery nozzle to provide a substantially uniform distribution of said particulate material in the cross direction of said fibrous web.

17. The method as recited in claim 15, wherein said end edge of said delivery nozzle flares out from said delivery conduit.

18. The method as recited in claim 17, further comprising the step of positioning said delivery nozzle to provide a substantially uniform distribution of said particulate material in the cross direction of said fibrous web.

19. The method as recited in claim 15, wherein said gaps in said end edge of said delivery nozzle are semi-circular in shape.

20. The method as recited in claim 19, further comprising the step of positioning said delivery nozzle to provide a substantially uniform distribution of said particulate material in the cross direction of said fibrous web.

21. The method as recited in claim 20, wherein said end edge of said delivery nozzle flares out from said delivery conduit.

22. The method as recited in claim 21, further comprising the step of positioning said delivery nozzle to provide a substantially uniform distribution of said particulate material in the cross direction of said fibrous web.

23. The method as recited in claim 15, wherein said gaps in said end edge of said delivery nozzle are triangular in shape.

24. The method as recited in claim 23, further comprising the step of positioning said delivery nozzle to provide a substantially uniform distribution of said particulate material in the cross direction of said fibrous web.

25. The method as recited in claim 24, wherein said end edge of said delivery nozzle flares out from the delivery conduit.

26. The method as recited in claim 25, further comprising the step of positioning said delivery nozzle to provide a substantially uniform distribution of said particulate material in the cross direction of said fibrous web.

27. The method as recited in claim 15, wherein said providing step (a) includes steps of:

generating a stream of conveying gas for entraining said particulate material; and, regulating a flow of said conveying gas to provide a gas flow velocity within the range of about 5 m/sec to about 45 m/sec.

28. The method as recited in claim 27, further comprising steps of:

providing said delivery gas stream; and, regulating a flow of said delivery gas stream to provide a velocity of gas flow within the range of about 5 m/sec to about 45 m/sec.

29. The method as recited in claim 28, further comprising a step of providing a selected, regulated mass flow rate of said particulate material within said supply stream.

30. The method as recited in claim 15, further comprising the step of controlling said flow of said particulate material from said delivery conduit and said delivery nozzle into said forming chamber.

31. The method as recited in claim 15, wherein said transferring step (b) comprises steps of:

delivering a controlled quantity of said particulate material to said delivery conduit; and, providing said delivery stream of gas at a selected velocity to move said particulate material through said delivery conduit.

32. The method as recited in claim 31, further comprising a step of directing a substantially continuous stream of particulate material into said web forming chamber.

33. The method as recited in claim 15, further comprising a step of directing an intermittent stream of particulate material into said web forming chamber.

34. The method as recited in claim 15, further comprising the step of directing a substantially continuous stream of particulate material into said web forming chamber.

35. The method as recited in claim 15, wherein said selective transferring step (b) comprises the steps of:

directing a first particulate material into said web forming chamber with a first transferring means; and, directing at least a second particulate material into said web forming chamber with a second transferring means.

36. The method as recited in claim 35, further comprising the step of directing a substantially continuous stream of particulate material into said web forming chamber.

37. A method for forming a substantially uniform distribution of particulate material in the cross-machine direction within a fibrous web, comprising the steps of:

(a) providing a gas entrained supply stream of said particulate material;

(b) transferring a selected quantity of said particulate material into a delivery gas stream to provide a flow of said particulate material through a delivery conduit and a delivery nozzle, including an end edge and having a oval shape including gaps on the end edge facing into a web forming chamber, into a web forming chamber;

(c) providing a flow of a selected fibrous material into said web forming chamber; and, (d) receiving said fibrous material and said particulate material on a foraminous forming layer located within said web forming chamber to produce said fibrous web which includes a substantially uniform distribution of said particulate material.

38. The method as recited in claim 37, further comprising the step of positioning said delivery nozzle to provide a substantially uniform distribution of said particulate material in the cross direction of said fibrous web.

39. The method as recited in claim 37, wherein said end edge of said delivery nozzle flares out from said delivery conduit.

40. The method as recited in claim 39, further comprising the step of positioning said delivery nozzle to provide a substantially uniform distribution of said particulate material in the cross direction of said fibrous web.

41. The method as recited in claim 37, wherein said gaps in said end edge of said delivery nozzle are semi-circular in shape.

42. The method as recited in claim 41, further comprising the step of positioning said delivery nozzle to provide a substantially uniform distribution of said particulate material in the cross direction of said fibrous web.

43. The method as recited in claim 42, wherein said end edge of said delivery nozzle flares out from said delivery conduit.

44. The method as recited in claim 43, further comprising the step of positioning said delivery nozzle to provide a substantially uniform distribution of said particulate material in the cross direction of said fibrous web.

45. The method as recited in claim 37, wherein said gaps in said end edge of said delivery nozzle are triangular in shape.

46. The method as recited in claim 45, further comprising the step of positioning said delivery nozzle to provide a substantially uniform distribution of said particulate material in the cross direction of said fibrous web.

47. The method as recited in claim 46, wherein said end edge of said delivery nozzle flares out from said delivery conduit.

48. The method as recited in claim 47, further comprising the step of positioning said delivery nozzle to provide a substantially uniform distribution of said particulate material in the cross direction of said fibrous web.

49. The method as recited in claim 37, wherein said providing step (a) includes steps of:
   generating a stream of conveying gas for entraining said particulate material; and,
   regulating a flow of said conveying gas to provide a gas flow velocity within the range of about 5 m/sec to about 45 m/sec.

50. The method as recited in claim 49, further comprising steps of:
   providing said delivery gas stream; and,
   regulating a flow of said delivery gas stream to provide a velocity of gas flow within the range of about 5 m/sec to about 45 m/sec.

51. The method as recited in claim 50, further comprising a step of providing a selected, regulated mass flow rate of said particulate material within said supply stream.

52. The method as recited in claim 37, further comprising the step of controlling said flow of said particulate material from said delivery conduit and said delivery nozzle into said web forming chamber.

53. The method as recited in claim 37, wherein said transferring step (b) comprises steps of:
   delivering a controlled quantity of said particulate material to said delivery conduit; and,
   providing said delivery stream of gas at a selected velocity to move said particulate material through said delivery conduit.

54. The method as recited in claim 53, further comprising a step of directing a substantially continuous stream of particulate material into said web forming chamber.

55. The method as recited in claim 37, further comprising a step of directing a substantially continuous stream of particulate material into said web forming chamber.

56. A method as recited in claim 37, further comprising the step of directing an intermittent stream of particulate material into said web forming chamber.

57. A method as recited in claim 37, wherein said selective transferring step (b) comprises the steps of:
   directing a first particulate material into said web forming chamber with a first transferring means; and,
   directing at least a second particulate material into said web forming chamber with a second transferring means.

58. A method as recited in claim 57, further comprising the step of directing a substantially continuous stream of particulate material into said web forming chamber.

59. A method for forming a substantially uniform distribution of particulate material in the cross-machine direction within a fibrous web, comprising the steps of:
   (a) providing a gas entrained supply stream of said particulate material;
   (b) transferring a selected quantity of said particulate material into a delivery gas stream to provide a flow of said particulate material through a delivery conduit and a delivery nozzle, including an end edge and a wedge member wherein said delivery nozzle is circular shaped, into a web forming chamber;
   (c) providing a flow of a selected fibrous material into said web forming chamber; and,
   (d) receiving said fibrous material and said particulate material on a foraminous forming layer located within said web forming chamber to produce said fibrous web which includes a substantially uniform distribution of said particulate material.

60. The method as recited in claim 59, further comprising the step of positioning said delivery nozzle to provide a substantially uniform distribution of said particulate material in the cross direction of said fibrous web.

61. The method as recited in claim 59, wherein said end edge of said delivery nozzle flares out from the delivery conduit.

62. The method as recited in claim 61, further comprising the step of positioning said delivery nozzle to provide a substantially uniform distribution of said particulate material in the cross direction of said fibrous web.

63. The method as recited in claim 59, wherein said providing step (a) includes steps of:
   generating a stream of conveying gas for entraining said particulate material; and,
   regulating a flow of said conveying gas to provide a gas flow velocity within the range of about 5 m/sec to about 45 m/sec.

64. The method as recited in claim 63, further comprising steps of:
   providing said delivery gas stream; and,
   regulating a flow of said delivery gas stream to provide a velocity of gas flow within the range of about 5 m/sec to about 45 m/sec.

65. The method as recited in claim 64, further comprising a step of providing a selected, regulated mass flow rate of said particulate material within said supply stream.

66. The method as recited in claim 59, further comprising the step of controlling said flow of said particulate material from said delivery conduit and said delivery nozzle into said web forming chamber.

67. The method as recited in claim 59, wherein said transferring step (b) comprises steps of:
   delivering a controlled quantity of said particulate material to said delivery conduit; and,
   providing said delivery stream of gas at a selected velocity to move said particulate material through said delivery conduit.

68. The method as recited in claim 67, further comprising a step of directing a substantially continuous stream of particulate material into said web forming chamber.

69. The method as recited in claim 59, further comprising a step of directing a substantially continuous stream of particulate material into said web forming chamber.

70. A method as recited in claim 59, further comprising the step of directing a intermittent stream of particulate material into said web forming chamber.

71. A method as recited in claim 59, wherein said selective transferring step (b) comprises the steps of:
   directing a first particulate material into said web forming chamber with a first transferring means; and,
   directing at least a second particulate material into said web forming chamber with a second transferring means.

72. A method as recited in claim 59, further comprising the step of directing a substantially continuous stream of particulate material into said web forming chamber.

* * * * *

UNITED STATES PATENT AND TRADEMARK OFFICE
CERTIFICATE OF CORRECTION

PATENT NO. : 6,207,099 B1 Page 1 of 1
DATED : March 27, 2001
INVENTOR(S) : John Anthony Rooyakkers et al.

It is certified that error appears in the above-identified patent and that said Letters Patent is hereby corrected as shown below:

Column 4,
Line 55, delete "410" and substitute -- 40 --.

Column 7,
Line 50, delete "10" after "of".

Column 12,
Line 38, insert -- in -- after "10".

Column 14,
Line 57, delete "arid" and substitute -- and --.

Signed and Sealed this

First Day of April, 2003

JAMES E. ROGAN
*Director of the United States Patent and Trademark Office*